United States Patent [19]

Ritscher et al.

[11] Patent Number: 5,210,254

[45] Date of Patent: May 11, 1993

[54] ACIDIC HALIDE NEUTRALIZATION IN ALKOXYSILANES

[75] Inventors: James S. Ritscher; Scot M. Turner, both of Marietta, Ohio

[73] Assignee: Union Carbide Chemicals & Plastics Technology Corporation, Danbury, Conn.

[21] Appl. No.: 861,273

[22] Filed: Mar. 31, 1992

[51] Int. Cl.$^5$ .............................. C07F 7/08; C07F 7/18
[52] U.S. Cl. ....................................... 556/466
[58] Field of Search ........................................ 556/466

[56] References Cited

U.S. PATENT DOCUMENTS

| 4,281,146 | 7/1981 | Ashby | 556/456 |
| 4,697,027 | 9/1987 | Sugihara et al. | 556/466 |
| 4,774,347 | 9/1988 | Marko et al. | 556/466 |
| 4,827,008 | 5/1989 | Gousetis et al. | 556/466 |
| 4,851,558 | 7/1989 | Nishida et al. | 556/471 |
| 4,861,907 | 8/1989 | Wright et al. | 556/419 |
| 4,956,486 | 9/1990 | Marko et al. | 556/466 |
| 4,962,221 | 10/1990 | Huntress et al. | 556/466 X |
| 5,084,588 | 2/1992 | Ocheltree et al. | 556/446 |
| 5,104,999 | 4/1992 | Satoh | 556/466 |

FOREIGN PATENT DOCUMENTS

| 223210 | 5/1987 | European Pat. Off. |
| 278726 | 8/1988 | European Pat. Off. |
| 282846 | 9/1988 | European Pat. Off. |
| 1115052 | 5/1968 | United Kingdom |

Primary Examiner—Paul F. Shaver
Attorney, Agent, or Firm—B. L. Deppenbrock

[57] ABSTRACT

A method for reducing the level of acidic halide contamination in alkoxysilanes by contacting the silane with a stoichiometric excess of (i) a basic reagent, such as in particular, a metal alkoxide and (ii) an acid salt.

14 Claims, No Drawings

ACIDIC HALIDE NEUTRALIZATION IN ALKOXYSILANES

FIELD OF THE INVENTION

This invention relates to a process for removing acidic halide contamination in alkoxysilanes, and in particular for removing residual acidic chloride in amino-substituted alkoxysilanes. The invention can reduce acidic halide contamination in the alkoxysilanes to less than 5 parts per million.

BACKGROUND OF THE INVENTION

Organic silanes having alkoxy or aryloxy substituents, and amino-substituted alkoxysilanes in particular, find use in a variety of applications such as in laundry additives, in caulking compound formulations, and as coupling agents between inorganic and organic surfaces such as in fiberglass products. Normally these silane compositions have a very pale yellow coloration.

Organic silanes having alkoxy or aryloxy substituents are typically prepared by reacting a halosilane with an alcohol or a phenol, commonly followed by treatment with an acid acceptor to neutralize residual acidic halide by-product. Amino-substituted alkoxysilanes can be prepared by the known reaction of a haloalkylalkoxysilane with a primary amine or a secondary amine. An acidic halide, such as hydrogen chloride, is also formed as an undesirable by-product of this reaction, and is typically removed as the hydrogen halide salt of an acid acceptor. As used herein the term "acidic halide" encompasses free residual hydrogen halide, bound hydrogen halide such as amine hydrohalide, silanic halide and mixtures thereof. Acidic halide contamination of the silane product is undesired for a variety of reasons, including increased corrosion of surfaces to which it is applied.

Many of the commonly-used inorganic alkaline neutralizing agents, such as the alkali metal hydroxides, are not used to remove acidic halide contaminants from silanes, particularly in the case of acidic halide contamination of alkoxysilanes. Such inorganic agents are not used because water is produced by the neutralization reaction and contributes to silane product degradation via a hydrolysis mechanism. The same is true for sodium carbonate and sodium bicarbonate which have been used in the past for neutralizing certain organosilanes. By-product water is a particularly troubling problem for alkoxysilanes having relatively high molecular weights since these alkoxysilanes produce a higher level of impurities when they undergo hydrolysis.

In the past, acidic halide contamination of alkoxysilanes generally, and particularly of amino-substituted alkoxysilanes, has been controlled by a post-reaction treatment with a strong base such as a metal alkoxide, e.g., sodium methoxide. Unfortunately, the quality of the silane product can be adversely affected by the level of metal alkoxide addition. If an insufficient amount of the metal alkoxide is added, an undesirably high residual halide level is encountered in the silane product. On the other hand, the addition of even a small excess of the metal alkoxide commonly causes an unacceptably severe and irreversible color development in the alkoxysilane product, particularly in those products having amine substitution. Such coloration is thought to be due to oxidation of the amine in the presence of the excess base. In addition, certain alkoxysilanes, such as vinyl alkoxysilanes, in the presence of metal alkoxide, in addition to color development, can also violently decompose during subsequent thermal treatment (e.g., distillation).

In light of the above, great care is exercised to obtain a proper neutralization end point when metal alkoxides are used for acidic halide removal. This degree of care is very inconvenient in an industrial context. Implementation of metal alkoxide neutralization, therefore, tends to be very time-consuming and often leads to the uneconomical reworking, e.g., distillation, or in the extreme, discarding of over-neutralized products.

One method which allows for the use of metal alkoxide without the need for assiduous control of the neutralization end point is described in U.S. Pat. No. 5,084,588. By the patented method for reducing the level of acidic halide contamination in alkoxysilanes, a metal alkoxide is provided to the system during a first stage treatment (partial neutralization) at a concentration of less than one molar equivalent based on the acidic halide content of the alkoxysilane. An alkali metal or alkaline earth metal salt of a weak acid is then used in excess to neutralize the remaining acidic halide and buffer the system without overneutralization. Suitable weak acids are those having a dissociation constant (Ka) between $10^{-15}$ and $10^{-2}$.

Notwithstanding the advance in the art made by said U.S. Pat. 5,084,588, there is a continuing need for a process which allows for the use of an excess of a basic reagent such as metal alkoxide and which readily achieves the desired neutralization of acidic halide without adversely affecting alkoxysilane product quality.

SUMMARY OF THE INVENTION

The present invention provides a process for reducing the level of acidic halide contaminants contained in alkoxysilanes such as, in particular, amino-substituted alkoxysilanes and vinylalkoxysilanes. The process comprises contacting the silane under substantially anhydrous conditions with (i) a base in a stoichiometric excess based on the level of acidic halide contained in the silane, and (ii) a stoichiometric excess of an acid salt based on the level of residual excess base provided to the system. Since the acid salt buffers the system back to neutrality from a basic condition, amino- and vinyl-substituted alkoxysilanes which are sensitive to prolonged contact with basic media can be brought to very low residual acidic halide contamination levels without adverse affects on product quality.

DETAILED DESCRIPTION OF THE INVENTION

In accordance with the teachings of this invention, an alkoxysilane containing acidic halide contaminant is neutralized with a stoichiometric excess of a base and an acid salt which buffers the reaction mixture to neutrality. The reaction is conducted under substantially anhydrous condition so as not to hydrolyze the silane. As used herein, "substantially anhydrous conditions" means that no water is intentionally added to or generated within the alkoxysilane-containing medium which is subjected to the treatment of this invention. While extraordinary efforts to dry equipment or chemicals are not required, the use of chemicals which generate or release water during the treatment are not employed. For example, alkali metal hydroxides are not suitable as the basic reagent because they form water upon reaction with acidic halide. Also, neither the basic reagent nor acid salt should be introduced to the system in hydrated form. Practice of the present invention can reduce acidic halide contamination within the silane to essentially neutral conditions. Generally less than 10 parts per million by weight (ppm) of acidic halide contaminants and usually less than 5 ppm of contamination remains after employing the present invention. The process of this invention is capable of reducing the acidic halide content of alkoxysilanes to levels that are not detectable by routine analytical techniques.

Although any base that does not form water upon neutralization can be utilized, the most attractive of such bases are those that are readily soluble within the alkoxysilane system. For this reason, metal alkoxides, and especially alkali metal alkoxides, are preferred. Illustrative metal alkoxides include sodium methoxide, sodium ethoxide, potassium methoxide, potassium ethoxide and magnesium ethoxide, of which sodium methoxide and sodium ethoxide are preferred. The metal alkoxide is preferably provided to the system as a solution in its corresponding alcohol. The metal alkoxide/alcohol solution in turn should correspond to the alkoxy group of the silane. This selection of reagents will prevent a trans-silyl-esterification reaction from occurring and the resulting production of various impurities. For example, sodium methoxide solution in methanol should be used with methoxysilanes.

The basic reagent such as, in particular, the metal alkoxide, is employed in an amount in excess of the stoichiometric amount required to neutralize the acidic halide content of the alkoxysilane. Generally a stoichiometric excess of base ranging from about 0.1 to about 200% is sufficient, with about 1 to about 50% excess preferred, and from about 5 to about 15% most preferred.

The alkoxysilane is also contacted with an excess of the acid salt which buffers the system to neutrality and thus maintains neutral conditions during downstream processing. The term "neutral conditions" as used herein means that neither an excess of acidic species nor an excess of basic species are present in the alkoxysilane system, i.e., an aqueous solution of the silane would have a pH of about seven, i.e., ±0.1 pH units. Similarly, the terms "acidic" and "basic" as used herein refer to a condition which if present in aqueous solution would provide a pH of less than or greater than seven, respectively. The excess of acid salt utilized is based upon the level of residual excess base in the system; that is, the level of the added stoichiometric excess of base remaining after neutralization of acidic halide contained in the alkoxysilane starting material. The selection of the acid salt is such that it is only sparingly soluble in the reaction medium so that the unneutralized excess of acid salt can be removed by filtration. In addition, the acid salt must be used in its anhydrous form and buffering of the excess basic reagent in the silane by the salt must not produce by-product water.

Illustrative acid salts are the monobasic and dibasic alkali metal phosphates which include sodium monohydrogen phosphate, potassium monohydrogen phosphate, sodium dihydrogen phosphate, potassium dihydrogen phosphate, and any combination thereof. Other suitable acid salts include anhydrous sodium and potassium citrates, tartrates, oxalates and bisulfates. The preferred acid salts are the monobasic and dibasic sodium and potassium phosphates including mixtures thereof.

The acid salts used to buffer the alkoxysilane-containing medium are provided in a stoichiometric excess relative to residual excess basic reagent, such as metal alkoxide, contained in the system. Generally a 10 to about 2500% stoichiometric excess of the acid salt is employed. Preferably an excess of 100 to 2000% of the acid salt is provided to the system, while especially preferred is a stoichiometric excess of the acid salt of from about 500 to about 1500%.

Treatment of the alkoxysilane may be accomplished simply by first adding the excess base to the silane under conditions effective to ensure contact between the acid halide contaminant and the base such as a metal alkoxide. In the broad practice of the present invention any procedure for contacting the base with the alkoxysilane can be used such as batch treatment, continuous mixing, countercurrent processing and the like. While treatment time depends somewhat on treatment temperature, contacting such as by mixing is normally continued for at least about one hour. Generally, contact times of greater than 24 hours should not be required. The temperatures at which the silane and base (e.g., metal alkoxide) are contacted can vary over a relatively wide range such as from ambient temperature (e.g., 22° C.) to elevated temperatures up to 200° C. or higher. With amino-substituted alkoxysilanes ambient temperatures are suitable, although usually the silane and basic reagent are contacted at an elevated temperature such as from about 50° to about 60° C. Also to be taken into account is the sensitivity of the silane, especially of vinylalkoxysilanes, to thermal treatment in the presence of a strong base such as metal alkoxide.

In addition to acidic halide contaminants, it may also be necessary to remove low boiling contaminants from the treated, i.e., neutralized, alkoxysilane, such as an alcohol, which may be added or generated during the neutralization process. If the neutralization reaction produces a volatile by-product, that also may be removed while the silane is at an elevated temperature. Preferably this is done prior to the solid/liquid separation, e.g., filtration, of the halide salt formed as a result of the neutralization of acidic halide with the basic reagent such as metal alkoxide. For example, such volatile by-products can be removed by a vacuum assisted distillation or stripping step, such as by heating the alkoxysilane under a vacuum for a time sufficient to remove any low boiling contaminants. However, in the broad practice of the present invention, such treatment to remove other volatile components can also be done after the solid/liquid separation.

The excess base and, in particular, the excess metal alkoxide is then neutralized with the added acid salt reagent such as the aforementioned alkali metal mono- and dibasic phosphates. In order to prevent the original acidic halide contamination from being simply replaced by another acidic contaminant as a consequence of the back neutralization of the basic reagent, the acid salt used must form an insoluble salt upon reaction with the basic reagent. When the basic reagent is a metal alkoxide, there also will necessarily be formed a stoichiometrically equivalent amount of the corresponding alcohol, which preferably is a volatile alcohol to facilitate removal. The insoluble salt is removed from the product by mechanical means and the alcohol by volatilization. Solids removal is best done using a simple filtration, although any solid/liquid separation technique, including centrifugation, decanting and the like, can be used. Preferably, the silane is stripped of alcohol and cooled prior to filtering to promote maximum precipitation (e.g., by crystallization) of the solid neutralization products.

Acid salts which are only sparingly soluble in the alkoxysilane at a reduced temperature, such as at about ambient temperature, e.g. 22°–25° C., but which exhibit greater solubility at higher temperatures are preferred. As used herein, the phrase "sparingly soluble" is defined as a solubility of less than about one gram per 100 grams of the alkoxysilane, preferably less than about 0.5 gram per 100 grams, and most preferably less than about 0.1. gram per 100 grams. In this way, any residual excess of the acid salt is easily removed from the treated alkoxysilane as a solid, along with the neutralized acidic halide, by filtration.

The temperature at which the overneutralized alkoxysilane and the acid salt are contacted is not narrowly critical. If the acid salt is added to the alkoxysilane as a dry solid, contacting can be performed at ambient temperatures and is preferably conducted at elevated temperatures of at least 100° C to facilitate maximum reactivity of the acid salt in the silane. When an amino-substituted alkoxysilane is contacted with a dry solid acid salt, such contacting is effected at an elevated temperature, preferably ranging from about 100° to about 120° C. Extreme temperatures which contribute to thermal degradation of the silane product, of course, must be avoided. If the acid salt is added to the silane as a slurry in a polar medium such as an alcohol, a lower treatment temperature may be used. The alcohol selected as a carrier solvent must not contribute to product degradation by an ester interchange with the alkoxysilane.

The manner in which the acid salt is contacted with the alkoxysilane-containing system is not critical. Sufficient contact can be achieved with agitation, packed columns, and the like. The time required for the acid salt to contact the residual excess base such as metal alkoxide is also not critical. The time required can range from one hour to several days. Generally, one day is more than sufficient for the acid salt to react with the residual excess base.

The present invention is useful for removing or reducing the level of acidic halide contamination in a wide variety of alkoxysilanes. Illustrative silanes include but are not limited to: methyltriphenoxysilane; vinyltriphenoxysilane; vinyltrimethoxysilane; vinyltriethoxysilane; chloropropyltrimethoxysilane; octyltriethoxysilane; N-($\beta$-aminoethyl)-$\gamma$-aminopropyltrimethoxysilane; N-[($\beta$-aminoethyl)-N'-$\beta$-aminoethyl]-$\gamma$-aminopropyltrimethoxysilane; N,N-bis(trimethoxy silylpropyl)amine; N-phenyl-$\gamma$-aminopropyltrimethoxysilane; N,N-diethyl-$\gamma$-aminopropyltrimethoxysilane; and the like. The present invention is especially useful for treating amino-substituted alkoxysilanes which are highly susceptible to oxidative degradation in the presence of strongly basic materials. Thus the present invention has particular utility for neutralizing amino-functional alkoxysilanes which experience severe color changes as a result of oxidative degradation in the presence of excess metal alkoxide. The present invention is also advantageously employed in neutralizing vinyl alkoxysilanes so as to minimize the possibility of violent decomposition during future processing.

The basic reagent and acid salt can be added to the acidic halide contaminated alkoxysilane simultaneously or sequentially in any order. For example, one sequence comprises the addition of a stoichiometric excess of metal alkoxide, at ambient or elevated temperature, based on the original acidic halide concentration. The metal alkoxide is best added to the alkoxysilane with continuous agitation of the reaction medium. Next a stoichiometric excess of the acid salt, based upon the amount of residual excess metal alkoxide, is added at ambient or elevated temperatures. In a particularly preferred embodiment the acid salt is an alkali metal monohydrogen phosphate or alkali metal dihydrogen phosphate and is added to the reaction mixture while using continuous agitation.

The second sequence is to charge the acid salt, preferably an alkali metal monohydrogen phosphate or an alkali metal dihydrogen phosphate, to the alkoxysilane medium at ambient or elevated temperatures prior to the neutralization step. Next, a stoichiometric excess of the basic reagent such as metal alkoxide is fed to the reaction medium, the said excess being based on halide analysis of the reaction medium. Due to the limited solubility of the metal phosphates in alkoxysilane media, the metal alkoxide, which is completely soluble in the silane, preferentially reacts with the acidic halide without neutralizing the alkali metal phosphate salts. It is only after the acidic halide such as hydrogen halide has been neutralized by the metal alkoxide that the residual excess of metal alkoxide reacts with (neutralizes) the metal phosphate acid salt.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE A

A 16 ounce glass container was equipped with a magnetic stirring bar. 475 grams of a 52% by weight solution of beta'-aminoethyl-beta-aminoethylgamma-aminopropyltrimethoxysilane in diethylenetriamine (DETA) was charged to the container. The silane solution was neutralized with a 5% stoichiometric excess (0.65 grams) of sodium methoxide solution (25% by weight sodium methoxide in methanol).

The overneutralized silane solution (105 g) was then transferred to a 250 ml flask and was subjected to vacuum stripping conditions of 140° C. and 85-95 mm Hg for 3.25 hours. The silane solution changed color from a very pale yellow to a dark yellow during this period of time.

EXAMPLE 1

A four ounce glass container was equipped with a magnetic stirring bar. Fifty (50) grams grams of a 50% by weight solution of beta'-aminoethyl-beta-aminoethyl-gamma-aminopropyltrimethoxy-silane DETA was charged to the container. The silane-containing solution was overneutralized with a 5% stoichiometric excess of sodium methoxide solution (25% by weight sodium methoxide in methanol) based on residual acid chloride analysis. Over-neutralization was confirmed in that 108 parts per million of residual soluble sodium remained after accounting for the contained soluble sodium chloride (comparing residual sodium and chloride analyses of the filtrate). This material was treated at ambient temperature for seventy hours with 1.0% (0.50 grams) of sodium dihydrogen phosphate (approximately 1700% stoichiometric excess acid salt). After filtration and analysis, the silane was found to have no residual acidic chloride nor any free sodium methoxide in solution based on chloride and sodium analysis. Furthermore, color of the silane was not affected by the above neutralization procedure and did not increase under vacuum stripping conditions at 130°–140° C. and 35–40mm Hg for approximately four hours.

EXAMPLE 2

Example 1 was repeated except that sodium monohydrogen phosphate was used as the buffering reagent instead of the dihydrogen compound. After filtration and analysis, no detectable acid chloride or residual metal alkoxide was present.

EXAMPLE 3

Example 1 was repeated except that the treatment time was reduced to eighteen hours. After filtration and analysis, no detectable acid chloride or metal alkoxide was present.

EXAMPLE 4

Example 3 was repeated except that sodium monohydrogen phosphate was used. After filtration and analysis, no detectable acid chloride or metal alkoxide was present.

EXAMPLE 5

Example 1 was repeated except that only 0.5% (0.25 grams) sodium dihydrogen phosphate was used with 18 hours of treatment. After filtration and analysis, no detectable acid chloride or residual metal alkoxide was present.

EXAMPLE 6

Example 5 was repeated except that sodium monohydrogen phosphate was used for 18 hours of treatment of the alkoxysilane. After filtration and analysis, no detectable acid chloride or residual metal alkoxide was present.

Examples 2 through 6 further demonstrate the efficacy of the present invention. Notwithstanding the use of a stoichiometric excess of metal alkoxide, the color of the silanes was not affected by the neutralization procedure and subsequent vacuum distillation.

EXAMPLE 7

A sixteen ounce glass container was equipped with a magnetic stirring bar. Vinyltrimethoxysilane (301.4 g) was overneutralized using 1.25 grams of a 25% by weight sodium methoxide in methanol solution. Titration revealed 0.0204 milliequivalents/g of base (0.11% sodium methoxide).

In a four ounce glass container 13.6 grams of the overneutralized silane was then contacted with 0.14 grams of sodium dihydrogen phosphate (92.4% by weight having a particle size greater than 297 microns) for 24 hours at ambient temperature. Filtration of the silane found no detectable residual base and no color change was noted.

EXAMPLE 8

Example 7 was repeated except that a pulverized form of sodium dihydrogen phosphate (48 mesh; less than 297 microns in size) was utilized. 9.3 grams of overneutralized vinyltrimethoxysilane from Example 7 was neutralized with 0.10 grams of pulverized sodium dihydrogen phosphate. After 2.5 hours of treatment, no detectable residual base was found.

This Example demonstrates that grinding of the acid salt results in a faster rate of back neutralization than unground acid salts.

We claim:

1. A process for removing acidic halide contained in an alkoxysilane which comprises contacting said alkoxysilane under substantially anhydrous conditions with (i) a base in a stoichiometric excess based on the level of said acidic halide, and (ii) a stoichiometric excess of an acid salt based on the level of residual excess base contained in the alkoxysilane.

2. The process of claim 1 wherein the base is a metal alkoxide.

3. The process of claim 2 wherein the metal alkoxide is an alkali metal alkoxide.

4. The process of claim 3 wherein the alkali metal alkoxide is selected from the group consisting of sodium methoxide, sodium ethoxide, potassium methoxide, potassium ethoxide and mixtures thereof.

5. The process of claim 1 wherein the stoichiometric excess of the base is 0.1 to 200% of the acidic halide content of the alkoxysilane.

6. The process of claim 1 wherein the acid salt is an alkali metal monobasic phosphate.

7. The process of claim 1 wherein the acid salt is an alkali metal dibasic phosphate.

8. The process of claim 1 wherein the acid salt is sodium monohydrogen phosphate, potassium monohydrogen phosphate, sodium dihydrogen phosphate, potassium dihydrogen phosphate or mixtures thereof.

9. The process of claim 2 wherein the acid salt is provided to the alkoxysilane before the metal alkoxide is provided.

10. The process of claim 2 wherein the metal alkoxide is provided to the alkoxysilane before the acid salt is provided.

11. The process of claim 2 wherein the metal alkoxide and acid salt are provided to the alkoxysilane simultaneously.

12. The process of claim 1 wherein the alkoxysilane is an amino-substituted alkoxysilane.

13. The process of claim 1 wherein the alkoxysilane is a vinylalkoxysilane.

14. A process for removing acidic halide contained in an alkoxysilane which comprises contacting said alkoxysilane under substantially anhydrous conditions with:
   a) a metal alkoxide selected from at least one member of the group consisting of sodium methoxide, sodium ethoxide, potassium methoxide, and potassium ethoxide, in a 0.1 to 200% excess of the amount of metal alkoxide required to substantially neutralize the acidic halide content of the alkoxysilane; and
   b) a stoichiometric excess of at least one member of an acid salt selected from the group consisting of sodium hydrogen phosphate, potassium hydrogen phosphate, sodium dihydrogen phosphate and potassium dihydrogen phosphate based on the level of residual excess metal alkoxide.

* * * * *